United States Patent [19]

Harada et al.

[11] Patent Number: 4,816,559

[45] Date of Patent: Mar. 28, 1989

[54] BIOLOGICALLY ACTIVE PEPTIDES TAN-866

[75] Inventors: Setsuo Harada, Kawanishi; Hideo Ono; Nozomi Katayama, both of Kobe, all of Japan

[73] Assignee: Takeda Chemical Industries, Ltd., Osaka, Japan

[21] Appl. No.: 71,264

[22] Filed: Jul. 8, 1987

[30] Foreign Application Priority Data

Jul. 8, 1986 [JP] Japan .................................. 61-160439
Apr. 1, 1987 [JP] Japan .................................. 62-82095

[51] Int. Cl.$^4$ .......................... C07K 7/50; C07K 1/12; C12P 21/00; C12P 21/04
[52] U.S. Cl. .................................... 530/317; 530/333; 435/68; 435/71
[58] Field of Search .................. 530/317, 333; 435/68, 435/71

[56] References Cited

PUBLICATIONS

Haskell et al., The Journal of Antibiotics, vol. XVI, No. 2, 1963, pp. 67–75.

Primary Examiner—Delbert R. Phillips
Assistant Examiner—Abdel A. Mohamed
Attorney, Agent, or Firm—Wenderoth, Lind & Ponack

[57] ABSTRACT

The iron-containing biologically active peptide TAN-866 produced by microorganisms belonging to the genus Pseudomonas and its iron free compounds have antibacterial activity mainly against gram-negative bacteria. These peptides can be used as a therepeutic agent for bacterial infections in mammals, domestic fowl, etc., caused by Pseudomonas aeruginosa. Further, TAN-866 and its deacyl compounds are also promising as the starting materials and intermediates for the synthesis of novel products.

5 Claims, 8 Drawing Sheets

BIOLOGICALLY ACTIVE PEPTIDES TAN-866

The present invention relates to novel peptides TAN-866 A, B, C or D or their related compounds useful as a therapeutic agent for bacterial infectious diseases, a method of producing them and a microorganism capable of producing at least one species of TAN-866 A, B, C and D.

As the compound most resembling to TAN-866 A, B, C and D in physico-chemical properties as described later can be mentioned succinimycin [Journal of Antibiotics, Vol. 16, p. 67 (1963)].

Owing to the development of therapeutics using antibiotics, diseases caused by bacteria have been overcome for the most part. There are, however, still some serious problems to be solved in the field of therapeutics of infectious diseases. For example, long-term or high-dose medication with conventional antibiotics causes changes in the flora of disease-causative bacteria (replacement of bacteria) and advent of drug-resistant bacteria (aquisition of drug-resistance) or increase of opportunistic microorganisms due to lowering of auto-immunity, resulting in an increase in diseases. In order to solve these problems, such substances as possessing novel structures and showing novel biological activities or intermediates for synthesizing them have always been demanded.

The present inventors isolated a great number of microorganisms from soils and plants for the purpose of searching for new substances, and investigated the substances produced by those microorganisms, finding that microbes of certain species produce a novel substance, that the microbes belong to the genus Pseudomonas, and that these microbes are capable of accumulating in a culture medium a substance possessing antibacterial activity against principally gram-negative bacteria. The present inventors isolated these substances, and, on the basis of their physicochemical properties as well as biological properties, they confirmed that these substances were novel and decided to name them TAN-866 A, B, C and D, respectively.

Based on these findings, the present inventors made further studies to complete the present invention.

Namely, the present invention relates to:

(1) A compound of the formula [I], or an iron-free compound thereof:

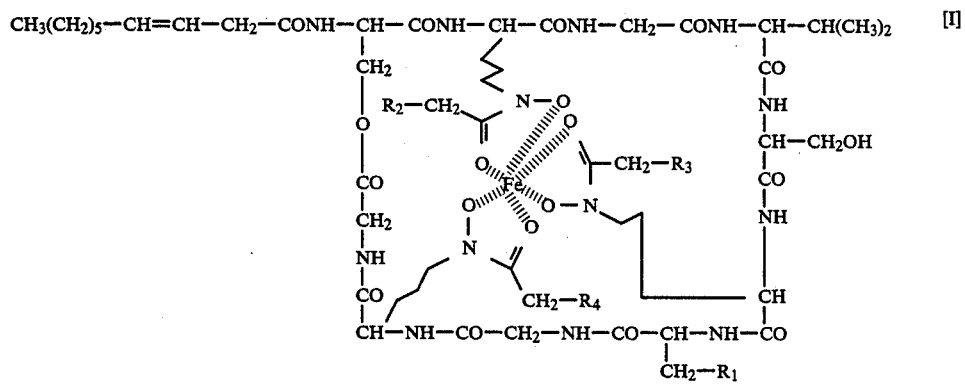

wherein $R_1$ is H or OH and each $R_2$, $R_3$ and $R_4$ is H or $CH_3$, (2) A method for producing a compound of the formula [I], or an iron-free compound thereof which comprises cultivating on a culture medium a microorganism belonging to the genus Pseudomonas and capable of producing at least one species of compounds represented by said formula to allow at least one species of said compounds to be accumulated in the medium, recovering thus-accumulated product, followed by subjecting the product to iron-liberation, upon necessary, (3) *Pseudomonas fluorescens* capable of producing a compound of the formula [I], (4) A compound of the formula [II], or an iron-free compound thereof:

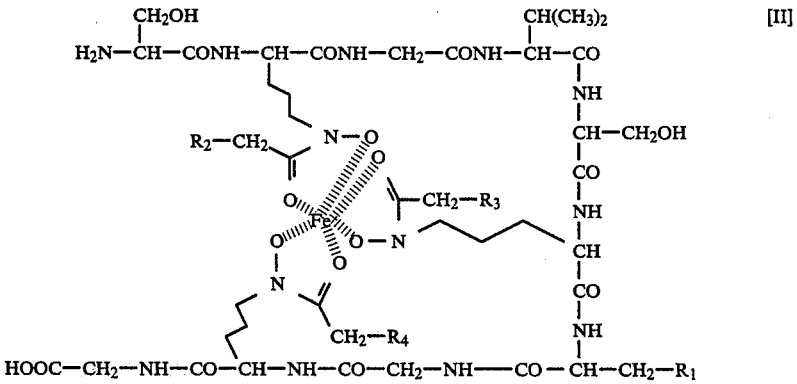

wherein $R_1$ is H or OH and each $R_2$, $R_3$ and $R_4$ is H or $CH_3$, and (5) A method of producing a compound of the formula [II] or an iron-free compound thereof, which comprises subjecting a compound of the formula [I] to hydrolysis by alkaline solutions for the cleavage of the lactone bond and to hydrolysis by the amidases for elimination of $CH_3(CH_2)_5—CH=CH—CH_2—CO—$ group, followed by subjecting the product to iron-liberation, upon necessary.

In the present specification, the compounds represented by the formula [I] are sometimes referred to briefly as TAN-866 A, B, C or D correspoonding to meanings of $R_1, R_2, R_3$ and $R_4$ as described below:

TAN-866 A: each $R_1, R_2, R_3$ and $R_4$ is H

TAN-866 B: $R_1$ is OH, and each $R_2, R_3$ and $R_4$ is H

TAN-866 C: $R_1$ is H, any two of $R_2, R_3$ and $R_4$ are H and the other is $CH_3$, and the retention time of HPLC mentioned later is 5.8 minutes.

TAN-866 D: $R_1$ is H, any two of $R_2, R_3$ and $R_4$ are H and the other is $CH_3$, and the retention time of HPLC mentioned later is 6.2 minutes.

TAN-866 A, B, C and D are sometimes generally called "TAN-866", and the compounds which are obtained by iron-liberation from the corresponding compounds of the formula [I] are sometimes referred to as "iron-free compounds". Further, the compounds represented by the formula [II] are sometimes referred to as "deacyl-TAN-866 A, B, C and D" and their corresponding "iron-free compounds".

BRIEF DESCRIPTION OF THE DRAWINGS

FIGS. 5, 6, 7, and 9 are respectively, IH NMR spectrum of TAN-866 A, B, C and D in $D_2O$.

Figure 1:
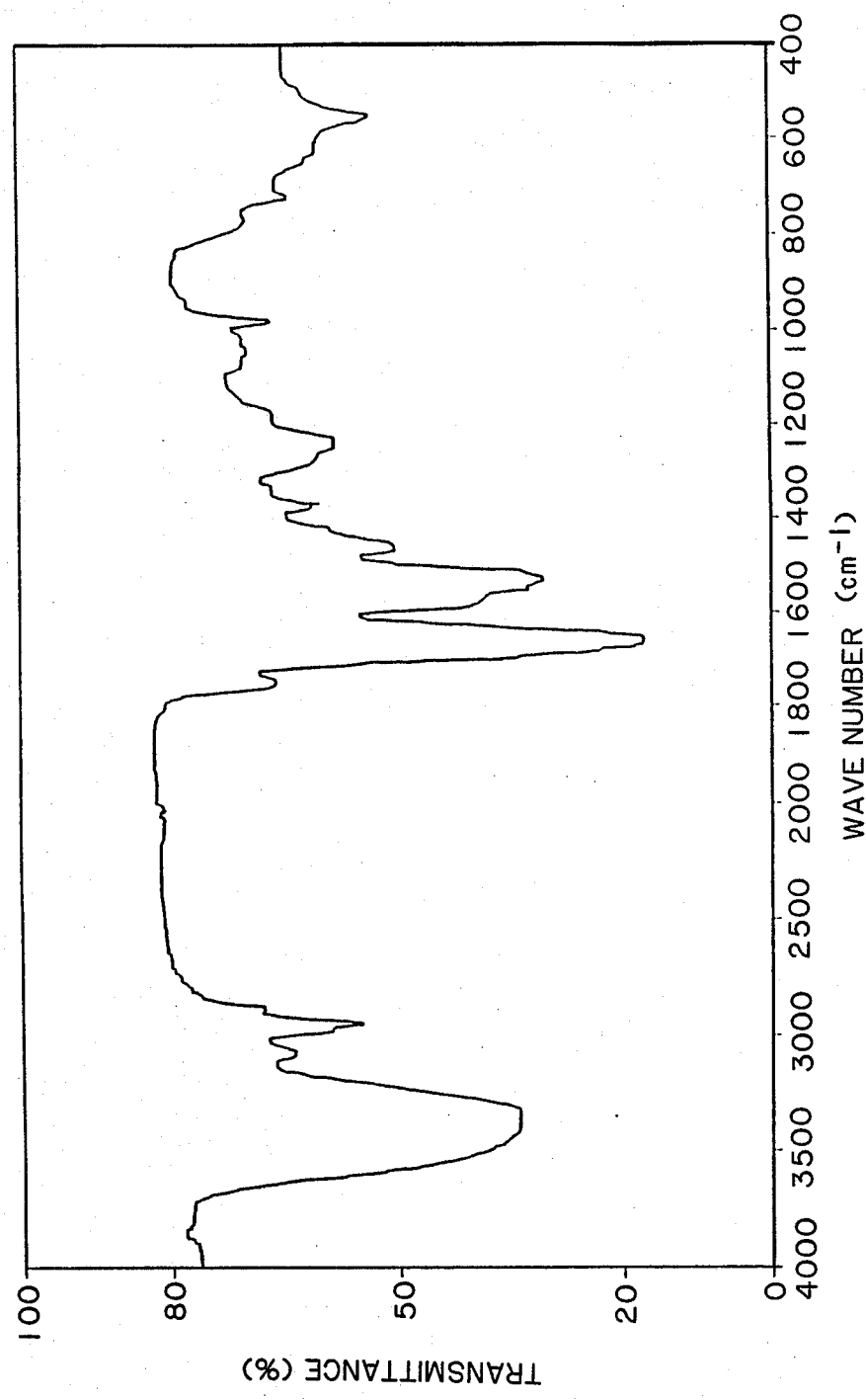
FIGS. 1, 2, 3 and 4 are, respectively, infra red absorption spectrum of TAN-866 A, B, C and D.

As the TAN-866 producing microbes employable in the present invention, any ones belonging to the genus Pseudomonas and capable of producing TAN-866 can be mentioned, for example, Pseudomonas fluorescens. More completely, Pseudomonas fluorescens YK-310 strain isolated from soils collected at Zentsuji, Kagawa Prefecture, Japan (hereinafter sometimes abbreviated as "strain YK-310").

Bacteriological characteristics of strain YK-310 are as follows:

(a) Morphology

Morphological characteristics were observed after incubation on a meat-extract agar slant medium at 24° C. for 5 days.

Cell shape and size: Rod, 0.6~1.2 μm diameter 0.8~2.1 μm length Motile with polar multitrichous flagellation; No sporulation; Gram-negative.

(b) Growth on various media

Observation was conducted for 1 to 14 days under incubation at 24° C.

1 Nutrient agar plate:

Colonies are colorless, opaque and circular. The colony surface is head-like. The colony margin is sinuous. No diffusible pigment is produced.

2 Nutrient agar slant:

Abundant, glossy and unfolded-cloth like, opaque and colorless.

3 Nutrient broth:

Grows in turbid suspension. Forms a thin pellicle. No precipitation appears.

4 Gelatin stab:

Good growth mainly on the upper portion. Liquefaction is observed.

5 Litmus milk:

Litmus-reduction activity is not observed. Peptonization activity is observed but coagulation is not.

(c) Physiological characteristics

1 Nitrate reduction: —
2 Denitrification: —
3 MR (methyl red) test: —
4 VP (Voges-Proskauer) test: —
5 Indole production: —
6 Hydrogen sulfide production (TSI agar and lead acetate paper): —
7 Starch hydrolysis: —
8 Citrate utilization (Koser's Christensen's and Simon's medium): +
9 Inorganic nitrogen source utilization:
  (i) Potassium nitrate: +
  (ii) Ammonium sulfate: +
10 Pigment production (King's A, King's B and Mannitol yeast extract agar medium): Production of yellowish green diffusible pigment is observed in King's B medium. No production of diffusible pigment is observed in either King's A medium or yeast extract agar medium.
11 Urease: +
12 Oxidase: +
13 Catalase: +
14 Conditions for growing:
  (i) pH: 4.7~10.0, optimally 7.2~8.4
    Medium: glucose 0.1%, yeast extract 0.01%, ammonium sulfate 0.1%, sodium chloride 0.1%, magnesium sulfate (7 hydrate) 0.05%, phosphate buffer 0.1M (sterilized separately)
  (ii) Temperature: 10°~34° C., optimally 10°~30° C.
    Medium: bouillon liquid medium
15 Oxygen demand: aerobic
16 O-F (oxidative-fermentative) test [Hugh.Leifson method]: oxidative
17 Acid and gas production from sugars and their utilization:

|  | Acid (Peptone Water) | Gas (Peptone Water) | Utilization (Davis' Medium) |
| --- | --- | --- | --- |
| L-arabinose | + | — | + |
| D-xylose | + | — | ± |
| D-glucose | + | — | + |
| D-mannose | + | — | + |
| D-fructose | — | — | + |
| D-galactose | + | — | + |
| Maltose | — | — | ± |
| Sucrose | — | — | + |
| Lactose | — | — | ± |
| Trehalose | — | — | — |
| D-sorbitol | — | — | ± |
| D-mannitol | — | — | + |
| Inositol | — | — | + |
| Glycerol | — | — | + |
| Starch | — | — | + |

18 G+C (guanine-cytosine) content of DNA: 65.9%±1.0% (Tm method)
19 Decomposition of polysaccharide:
  carboxymethyl cellulose: —
  colloidal chitin: —
  sodium arginate: —
20 Decomposition of Tween 80: +

Strain YK-310 having the afore-mentioned bacteriological characteristics was collated with bacterial species described in Bergey's Manual of Determinative Bacteriology, 8th edition, International Journal of Systematic Bacteriology, Vol. 30, pp. 225~420 (1980) and ibid Vol. 32, pp. 146~149; this strain was assumed as belonging to the genus Pseudomonas, based on the following characteristics, i.e. the strain is an gram-negative rod, motile with multitrichous flagellation, aerobic, catalase-positive and oxidase-positive, and the G+C content of its DNA is 65.9±1.0 mole %.

According to said Bergey's Mannual of Determinative Bacteriology, the genus Pseudomonas is divided into four sections, i.e. Sections I, II, III and IV, by its characteristics concerning requirement of growth factors, intracellular accumulation of poly-$\beta$-hydroxybutyrate, utilization of DL-arginine and growth at 40° C.

Table 1 shows the characteristics of the strain YK-310 as obtained by further experiments.

TABLE 1

| Characteristics of Strain YK-310 | |
|---|---|
| Tests | Result* |
| Poly-$\beta$-hydroxybutyrate accumulation | − |
| Arginine dihydrase | + |
| Pigment production: | |
| King's A medium | − |
| King's B medium | + |
| Denitrificaition | − |
| Gelatin hydrolysis | + |
| Poly-$\beta$-hydroxybutyrate hydrolysis | − |
| Utilization of carbon sources**: | |
| Sucrose | + |
| L-Arabinose | + |
| Propionate | − |
| Butyrate | − |
| Propylene glycol | − |
| Ethanol | − |

*+: Positive, −: Negative
**Stainer's medium [described in Journal of General Microbiology, Vol. 43, pp. 159~271 (1966)] was used.

It was considered appropriate that the strain YK-310 belongs to the Section I on the basis of the facts that the strain has no auxotrophy and does not accumulate poly-$\beta$-hydroxybutyrate intracellularly.

Ten species are included in Section I. As the strain YK-310 produces fluorescent pigment and possesses arginine dihydrolase, the strain YK-310 was considered as belonging to any of Pseudomonas aeruginosa, Pseudomonas putida, Pseudomonas fluorescens, Pseudomonas chlororaphis and Pseudomonas aureofaciens.

The strain YK-310 was different from Pseudomonas aeruginosa and Pseudomonas chlororaphis in denitrification. It was also different from Pseudomonas putida in hydrolysis of gelatin and utilization of sucrose, and from Pseudomonas aureofaciens in producibility of non-fluorescent pigment and reduction of nitrate. The characteristics of the strain YK-310 were in good agreement with those of Pseudomonas fluorescens. Therefore, the strain YK-310 was identified as Pseudomonas fluorescens, and designated Pseudomonas fluroescens YK-310.

The above-mentioned Pseudomonas fluorescens YK-310 has been deposited at Fermentation Research Institute, Agency of Industrial Science and Technology, Ministry of International Trade and Industry (FRI, 1-3, Higashi-1 Chome, Yatabe-cho, Tsukuba-gun, Ibaraki Prefecture, Japan) under the accession number of FERM P-8833 as from July 3, 1986, and also at the Institute for Fermentation, Osaka (IFO, 2-17-85, Juso-honmachi, Yodogawa-ku, Osaka, Japan) under the accession number of IFO 14516 since June 24, 1986. The above deposition at FRI has been converted to a deposit under the Budapest Treaty under the accession number of FERM BP-1369.

Bacteria belonging to the genus Pseudomonas used in method of the present invention are, in general, very susceptible to mutagens, e.g., it can be varied easily by mutations using ultraviolet ray, X-ray, chemicals (e.g. nitrosoguanidine and ethyl methanesulfonate), etc.; and strains which can be used in the present invention include all mutants capable of producing TAN-866.

In the incubation of TAN-866-producing bacteria, substances which can be assimilated by the bacteria are used properly as carbon sources: glucose, fructose, galactose, soluble.starch, dextrin, oils and fats (e.g. soybean oil, olive oil, etc.), organic acids (e.g. citric acid, succinic acid, gluconic acid, etc.), etc. As nitrogen sources, organic nitrogen compounds such as soybean flour, cotton seed powder, corn.gluten.meal, dried yeast, yeast extract, meat extract, peptone, urea, etc. Inorganic salts such as sodium chloride, potassium chloride, calcium carbonate, magnesium sulfate, potassium primary phosphate and potassium secondary phosphate, which are essential to ordinary bacterial cultures, can be properly used singly or in combination.

Heavy metals such as ferrous sulfate and copper sulfate, and vitamins such as vitamin $B_1$ and biotin, are supplemented when required. Antifoaming agents such as silicone oil and polyalkylene glycol ether, and surface active agents, can also be added to the medium. Further, any other organic or inorganic substance which facilitate the growth of microbes and thus promote TAN-866 production can also be added upon necessity.

As for culture methods, ordinary production methods for antibiotics can be applied; either solid or liquid culture may be applicable. In the case of liquid cultures, stationary cultures, agitating cultures, shaking cultures, aeration cultures, etc. can be optionally conducted; agitating culture under aeration is especially preferable. Culture temperature is preferably in a range of about 15° C.~32° C., pH is in a range of about 5~8, and the culture is conducted for approximately 8~168 hours, preferably 24~144 hours.

For harvesting the objective TAN-866 from cultures, separation methods which are usually used to isolate metabolites produced by microbes from their cultures can properly be used. For example, TAN-866, which is a neutral substance, is contained mainly in culture filtrate, and it is recovered advantageously by, among others, the following procedures. Namely, the whole culture broth, after addition of a filter aid, is subjected to filtration or centrifugation to remove cells, and the resulting culture filtrate is put in contact with a water-immiscible organic solvent to extract the active components, or the culture liquid is put in contact with a proper carrier to adsorb active components in the filtrate and recover the objective products by desorbing with an appropriate solvent fractionally by means of chromatography. The carrier to be employed advantageously includes silica gel, cellulose, adsorptive resins, etc. which utilize the difference of adsorbability among compounds, or molecular sieve carriers which utilize the difference of molecular weight among compounds. Elutions which can be used in a proper combination to elute objective compounds from these carriers include organic solvents, water-containing solutions of water-soluble organic solvents, e.g. hydrous acetone, hydrous alcohols, etc., though the combination varies with types and properties of carriers. Depending on cases, crude products thus obtained chromatographycally are subjected to reversed-phase HPLC for separation to perform further purification.

To describe in more detail, use is made of, as the carrier, for example, Amberlite XAD-II (Rohm & Haas Co., USA), Diaion HP-10, HP-20 and SP-207 (Mitsubishi Chemical Industries, Ltd., Japan) etc. to adsorb the active substances in the filtrate, then the thus-adsorbed materials are eluted with a mixture of an organic solvent and an aqueous solution, i.e. a mixture of acetone or methanol or the like and water or an aqueous or buffer solution containing acids or salts.

TAN-866 can also be extracted from its aqueous solution with an organic solvent which can be separated from water, e.g. n-butanol, iso-butanol, n-amyl alcohol, iso-amyl alcohol, etc. Further, TAN-866 can be adsorbed on a carrier such as silica gel or molecular sieve type carrier e.g. Kieselgel 60 (E. Merck AG, W. Germany) or molecular sieve carriers such as Sephadex LH-20 (Pharmacia Fine Chemicals, Sweden) and then thus-adsorbed material can be eluted with a suitable organic solvent, for example, chloroform, ethyl acetate, acetone, alcohols (e.g. methanol, etc.) or a mixture thereof.

As the column to be used for reversed phase HPLC, use is made of, for example, YMC gel (Yamamura Chemical Laboratories, Japan). As the mobile phase, use is made of a mixture of methanol or acetonitrile, etc. and a buffer solution. For purification of TAN-866, besides combinations of the above-mentioned procedures, an optional combination of concentration, crystallization, lyophilization, etc. which are conventionally used in laboratories can be applied.

TAN-866 presents in the culture broth as a trivalent iron complex, and it can be purified and isolated as it is by means of procedures described as above. Thus-isolated iron complex can be converted to TAN-866 iron-free compound by using a conventional iron ion removing agent such as 8-hydroxyquinoline, or a strong cation-excahnge resin such as Amberlite IR-120 (Rohm & Haas Co., USA), Dowex 50W (Dow Chemical Co., USA), etc. Addition of a trivalent iron compound, e.g. ferric chloride or ferric sulfate or the like to an aqueous solution of the free compound of TAN-866 affords TAN-866.

Physical and chemical properties of TAN-866 A, B, C and D, which were obtained in Example 1 and 2 to be shown later are as follows:

TAN-866A (1) Appearance: Reddish orange solid
(2) Specific rotation: $[\alpha]_D^{25} + 170°$ (c=0.1, in water)
(3) Molecular formula: $C_{51}H_{82}N_{13}O_{19}Fe$
(4) Elemental analysis (%): Samples were subjected to analysis after drying on phosphorus pentoxide at 40° C. for 6 hours. (calculated as containing 5 moles of water)

|  | C | H | N | O | Fe |
|---|---|---|---|---|---|
| Found: | 45.86 | 6.67 | 13.68 |  | 5.0 |
| Calcd.: | 46.15 | 6.99 | 13.72 | 28.93 | 4.21 |

(5) Molecular weight: m/z 1237(M+H)+ (SI-MS method)
(6) Ultraviolet and visible (UV & VS) absorption spectrum (in water): $\lambda_{max}$ 423±3 nm ($E_1^{1\%}{}_{cm}=25\pm5$)
(7) Infrared (IR) absorption spectrum: in KBr Main absorptions are as follows. (FIG. 1) 3350, 2950, 1750, 1660, 1530, 1460, 1380, 1240, 1040, 980, 720, 550 (cm$^{-1}$)
(8) Composition of constituent amino acids:
  (a) Samples hydrolized in 6N HCl at 110° C. for 15 hours: serine (2 moles), glycine (3 moles), alanine (1 mole). valine (1 mole)
  (b) Samples hydrolized in 57% hydriodic acid at 100° C. for 15 hours: serine (2 moles), glycine (3 moles), alanine (1 mole), valine (1 mole), ornithine (3 moles)
(9) HPLC:
Column: YMC-PAK A312 (Yamamura Chemical Laboratories)
Mobile phase: 36% CH$_3$CN water,
Flow rate: 2 ml/min. Rt=5.3 (min.)
(10) Solubility:
Soluble: water, dimethyl sulfoxide, methanol
Sparingly soluble: n-hexane, diethyl ether
(11) Classification of substance: neutral substance

TAN-866B (1) Appearance: Reddish orange solid
(2) Specific rotation: $[\alpha]_D^{25} + 164°$ (c=0.1, in water)
(3) Molecular formula: $C_{51}H_{82}N_{13}O_{20}Fe$
(4) Elemental analysis (%): Samples were subjected to analysis after drying on phosphorus pentoxide at 40° C. for 6 hours. (calculated as containing 6 moles of water)

|  | C | H | N | O | Fe |
|---|---|---|---|---|---|
| Found: | 45.07 | 6.88 | 13.47 |  | 3.0 |
| Calcd.: | 45.00 | 6.96 | 13.38 | 30.56 | 4.10 |

Figure 2:
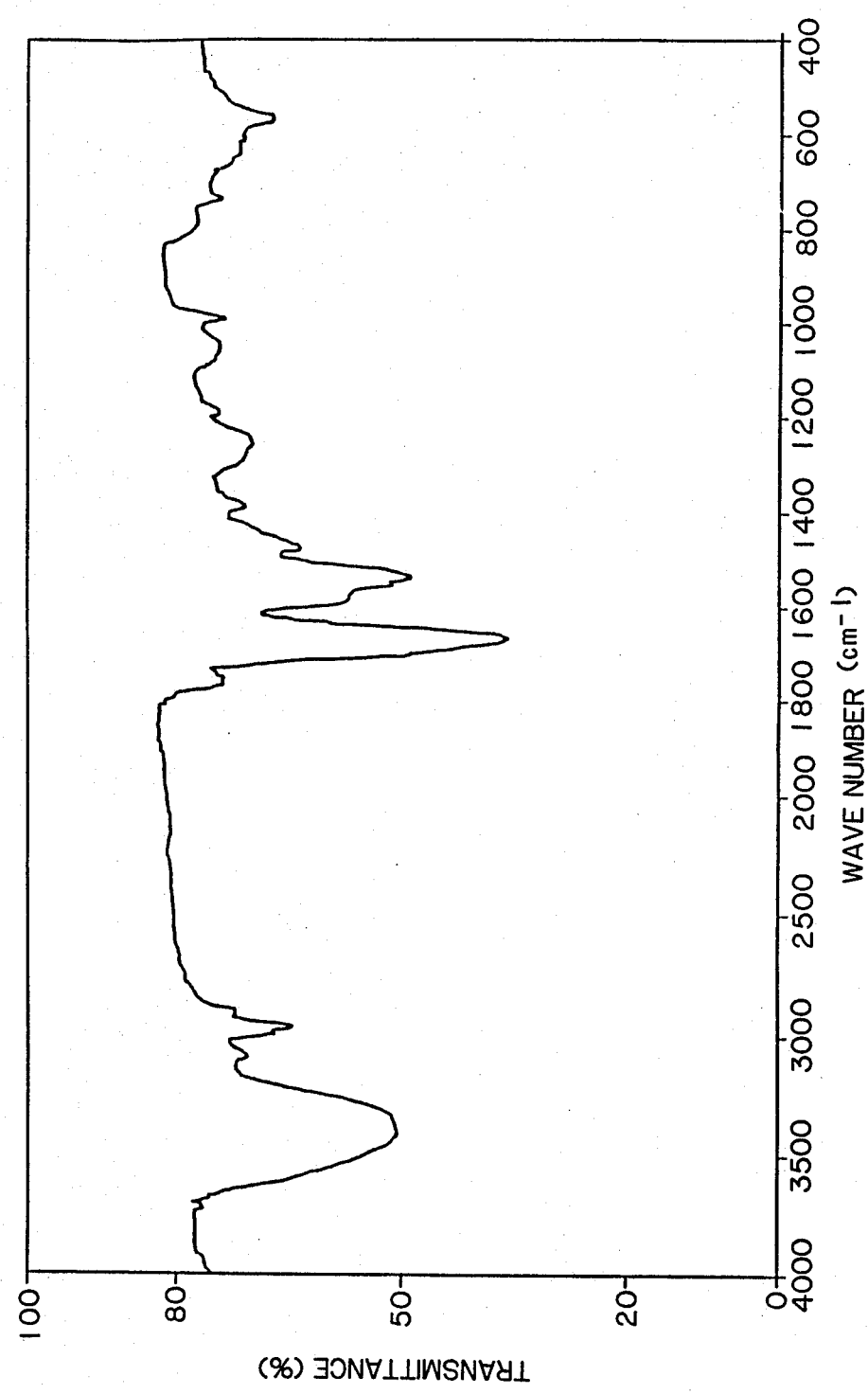

(5) Molecular weight: m/z 1253(M+H)+ (SI-MS method)
(6) Ultraviolet and visible (UV & VS) absorption spectrum (in water): $\lambda_{max}$422±3 nm ($E_1{}_{cm}^{1\%}=20\pm5$)
(7) Infrared (IR) absorption spectrum: in KBr Main absorptions are as follows. (FIG. 2) 3370, 2930, 1750, 1660, 1530, 1470, 1380, 1230, 1040, 980, 730, 560 (cm$^{-1}$)
(8) Composition of constituent amino acids:
  (a) Samples hydrolyzed in 6N HCl at 110° C. for 15 hours: serine (3 moles), glycine (3 moles), valine (1 mole)
  (b) Samples hydrolized in 57% hydriodic acid at 100° C. for 15 hours: serine (3 moles), glycine (3 moles), valine (1 mole), ornithine (3 moles)
(9) HPLC:
Column: YMC-PAK A312 (Yamamura Chemical Laboratories)
Mobile phase: 36% CH$_3$CN Water
Flow rate: 2 ml/min. Rt=4.7 (min.)
(10) Solubility:
Soluble: water, dimethyl sulfoxide, methanol
Sparingly soluble: n-hexane, diethyl ether
(11) Classification of substance: neutral substance

TAN-866C (1) Appearance: Reddish orange solid
(2) Specific rotation: $[\alpha]_D^{25} + 187°$ (c=0.1, in water)
(3) Molecular formula: $C_{52}H_{84}N_{13}O_{19}Fe$
(4) Elemental analysis (%): Samples were subjected to analysis after drying on phosphorus pentoxide at 40° C. for 6 hours. (calculated as containing 4 moles of water)

|  | C | H | N | O | Fe |
|---|---|---|---|---|---|
| Found: | 47.29 | 7.12 | 13.88 |  | 4.3 |

|         | C     | H    | N     | O     | Fe   |
|---------|-------|------|-------|-------|------|
| Calcd.: | 47.20 | 7.01 | 13.76 | 27.81 | 4.22 |

(5) Molecular weight: m/z 1251(M+H)+ (SI-MS method)

(6) Ultraviolet and visible (UV & VS) absorption spectrum (in water): $\lambda_{max}$423±3 nm ($E_{1\,cm}^{1\%}$=24±5)

Figure 3:
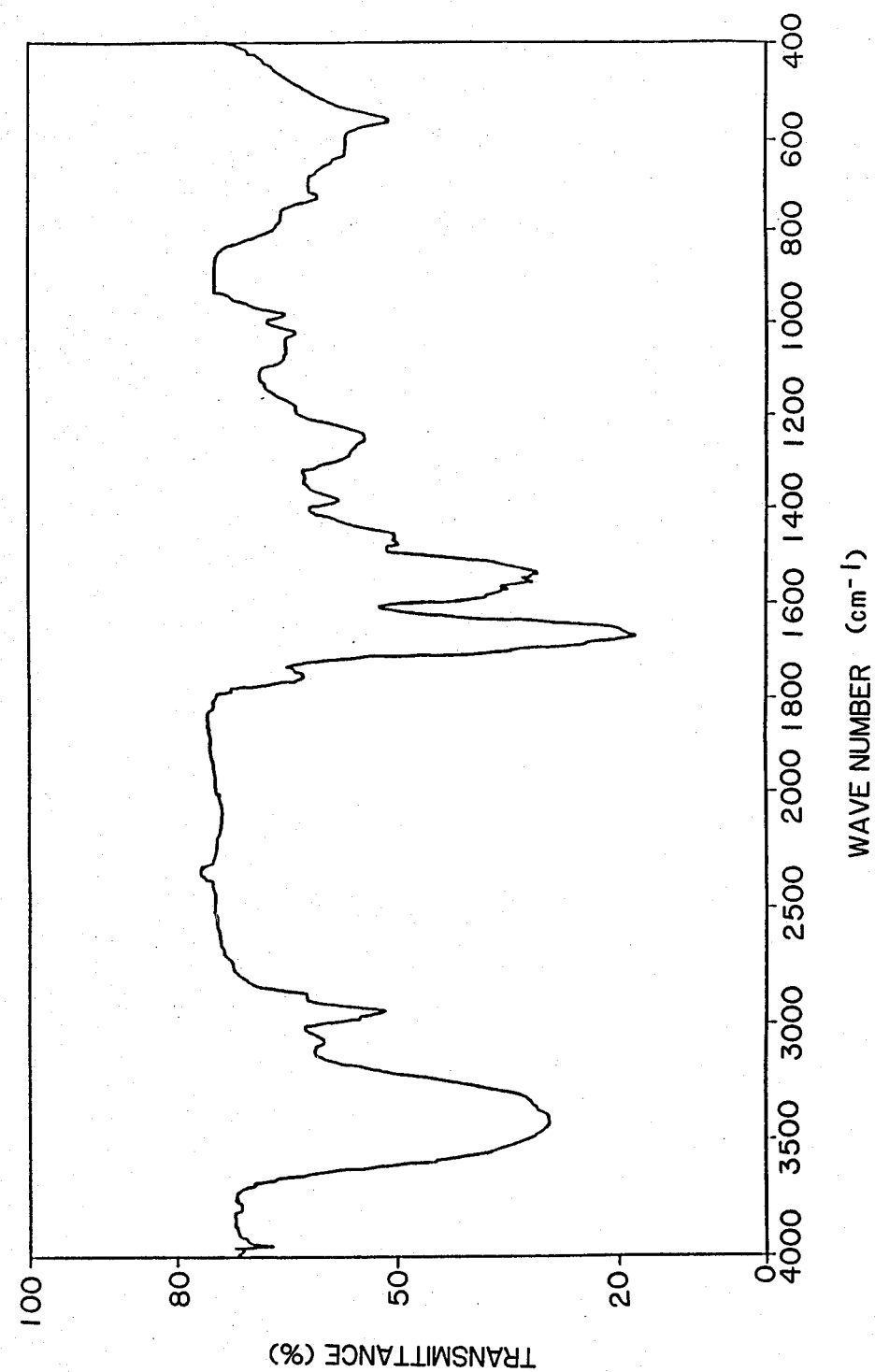

(7) Infrared (IR) absorption spectrum: in KBr Main absorptions are as follows. (FIG. 3) 3400, 2930, 1750, 1660, 1540, 1470, 1380, 1240, 1020, 980, 730, 560 (cm$^{-1}$)

(8) Composition of constituent amino acids:
(a) Samples hydrolyzed in 6N HCl at 110° C. for 15 hours: serine (2 moles), glycin (3 moles), alanine (1 mole), valine (1 mole)
(b) Samples hydrolized in 57% hydriodic acid at 100° C. for 15 hours: serine (2 moles), glycin (3 moles), alanine (1 mole), valine (1 mole), ornithine (3 moles)

(9) HPLC:
Column: YMC-PAK A312 (Yamamura Chemical Laboratories)
Mobile phase: 36% CH$_3$CN water
Flow rate: 2 ml/min. Rt=5.8 (min.)

(10) Solubility:
Soluble: water, dimethyl sulfoxide, methanol
Sparingly soluble: n-hexane, diethyl ether

(11) Classification of substance: neutral substance

TAN-866D (1) Appearance: Reddish orange solid
(2) Specific rotation: $[\alpha]_D^{25}$+176° (c=0.1, in water)
(3) Molecular formula: $C_{52}H_{84}N_{13}O_{19}Fe$
(4) Elemental analysis (%): Samples were subjected to analysis after drying on phosphorus pentoxide at 40° C. for 6 hours. (calculated as containing 4 moles of water)

|         | C     | H    | N     | O     | Fe   |
|---------|-------|------|-------|-------|------|
| Found:  | 47.10 | 7.07 | 13.80 |       | 4.2  |
| Calcd.: | 47.20 | 7.01 | 13.76 | 27.81 | 4.22 |

(5) Molecular weight: m/z 1251(M+H)+ (SI-MS method)

(6) Ultraviolet and visible (UV & VS) absorption spectrum (in water): $\lambda_{max}$423±3 nm ($E_{1\,cm}^{1\%}$=22 ±5)

Figure 4:
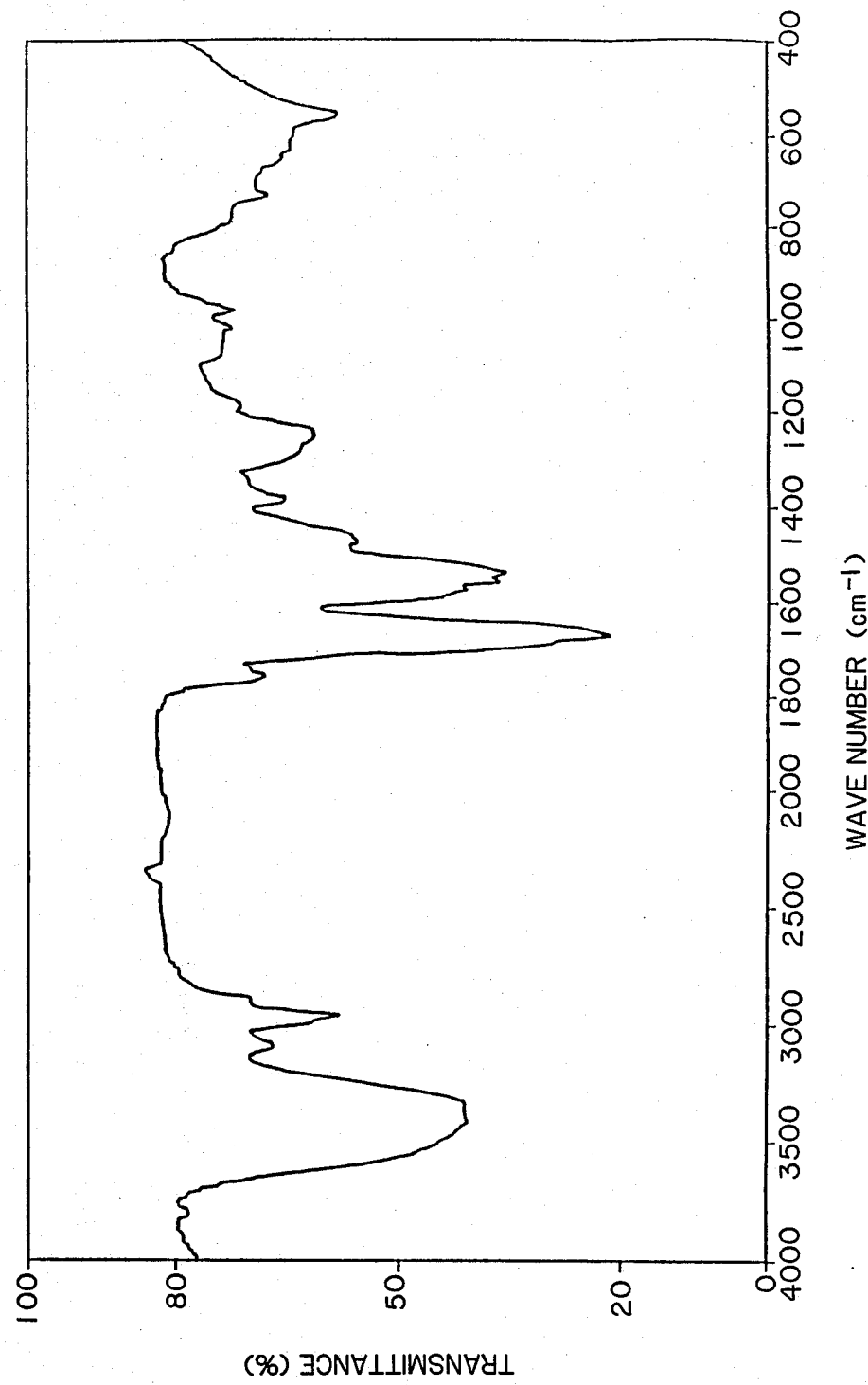
Figure 5:
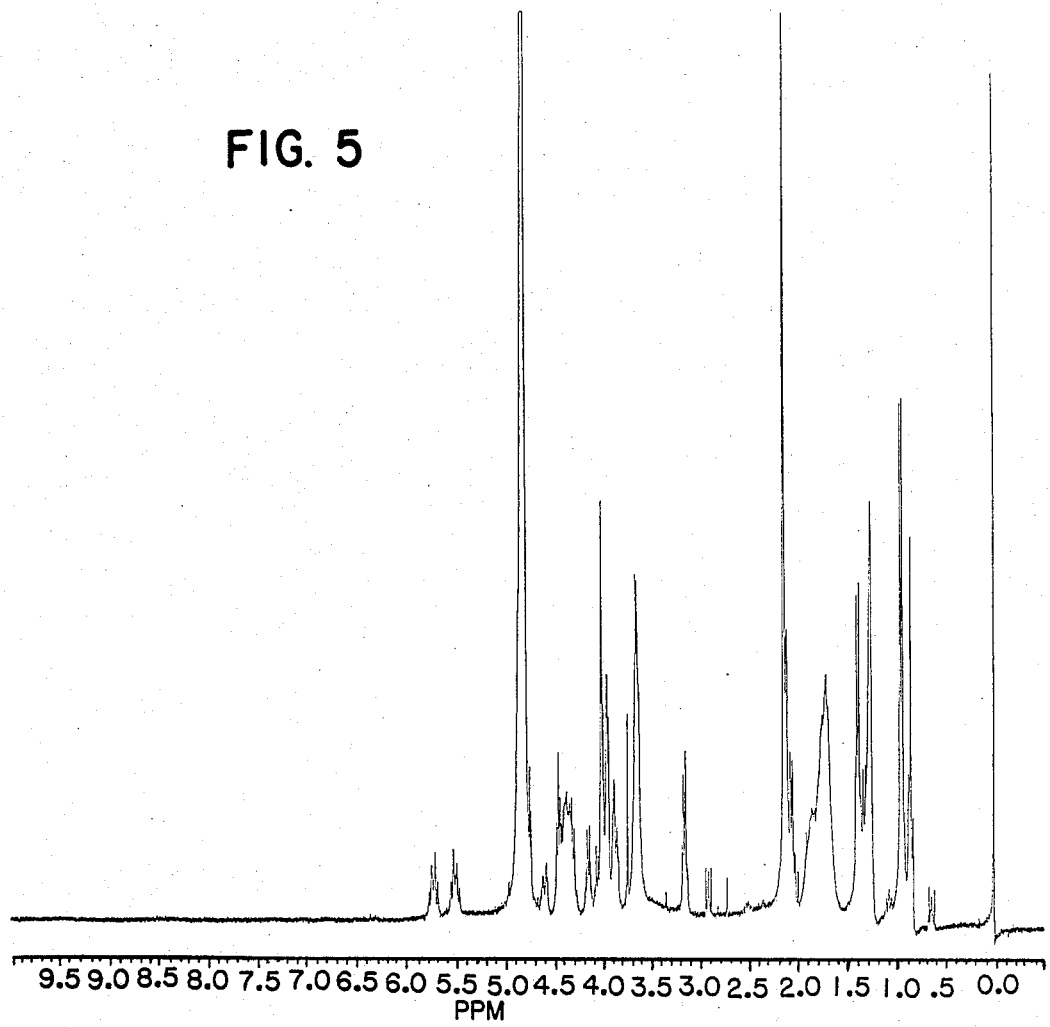
Figure 6:
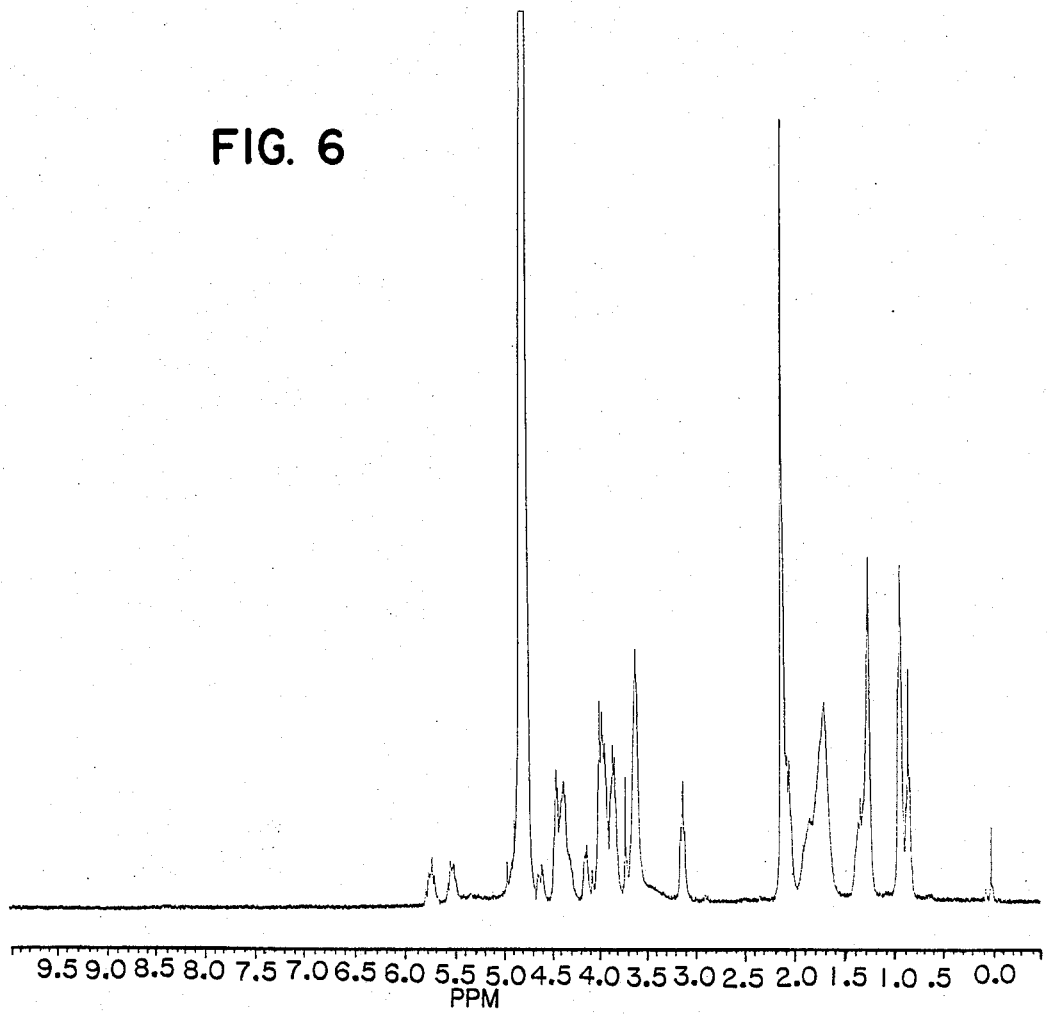
Figure 7:
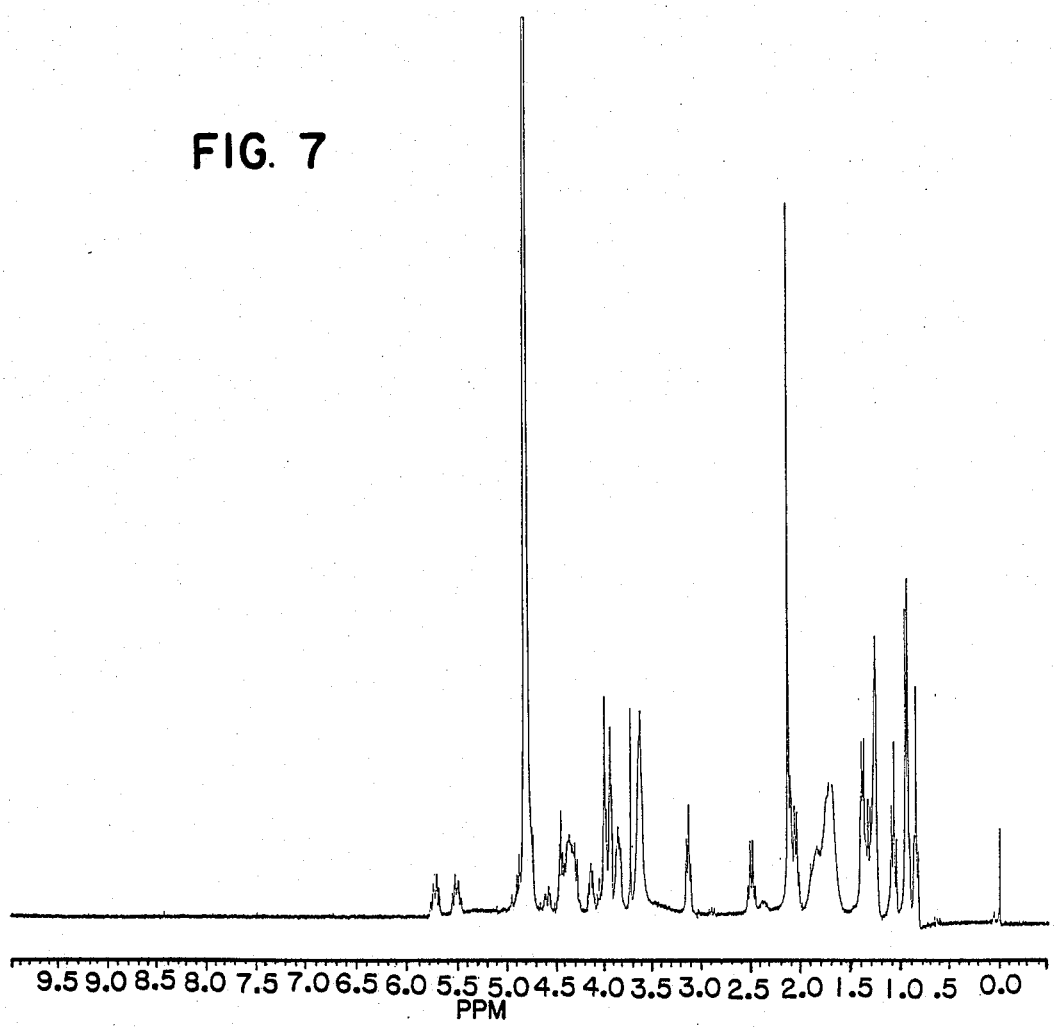
Figure 8:
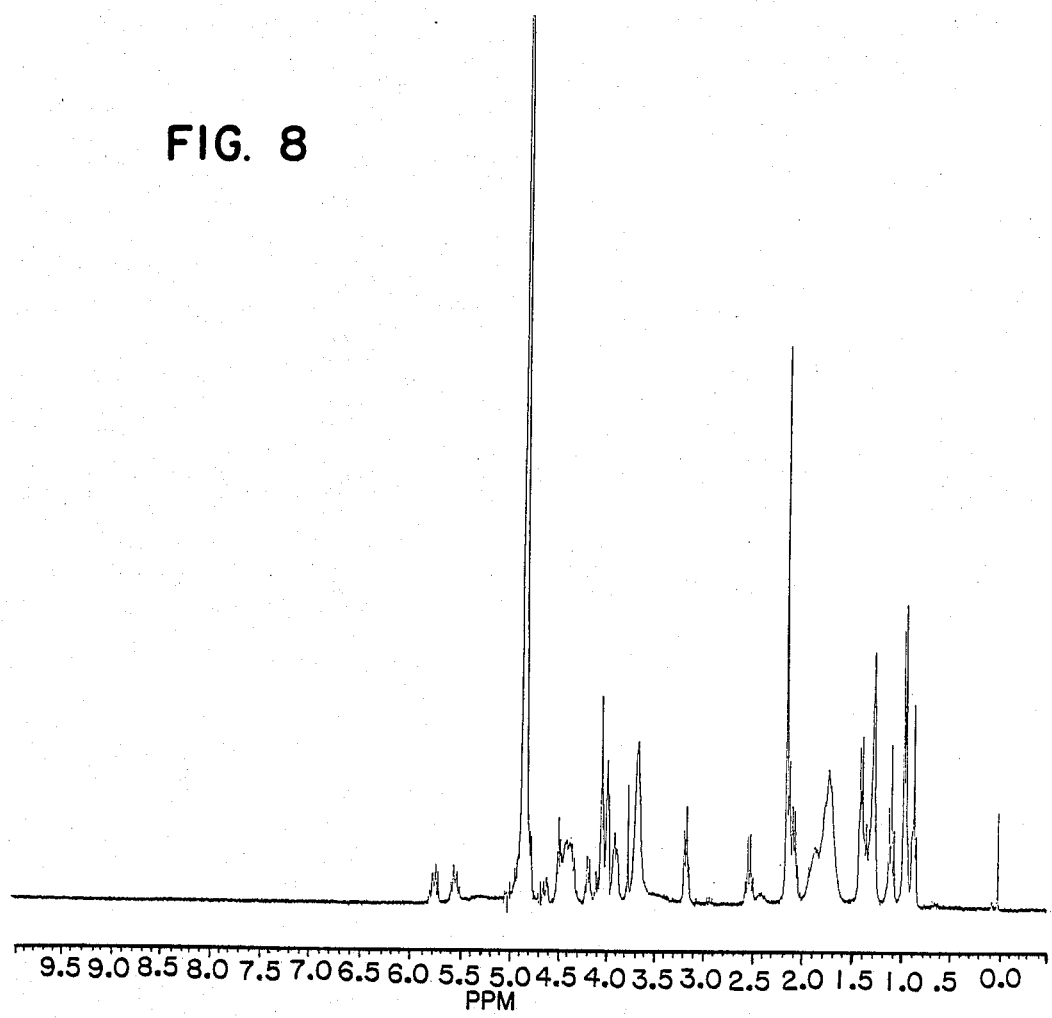

(7) Infrared (IR) absorption spectrum: in KBr Main absorptions are as follows. (FIG. 4) 3400, 2940, 1750, 1660, 1540, 1370, 1240, 1010, 980, 730, 560 (cm$^{-1}$)

(8) Composition of constituent amino acids:
(a) Samples hydrolized in 6N HCl at 110° C. for 15 hours: serine (2 moles), glycin (3 moles), alanine (1 mole), valine (1 mole)
(b) Samples hydrolized in 57% hydriodic acid at 100° C. for 15 hours: serine (2 moles), glycin (3 moles) alanine (1 mole), valine (1 mole), ornithine (3 moles)

(9) HPLC:
Column: YMC-PAK A312 (Yamamura Chemical Laboratories)
Mobile phase: 36% CH$_3$CN water
Flow rate: 2 ml/min. Rt=6.2(min.)

(10) Solubility:
Soluble: water, dimethyl sulfoxide, methanol
Sparingly soluble: n-hexane, diethyl ether

(11) Classification of substance: neutral substance

Further, the $^1$H NMR spectra of TAN-866 A, B, C and D in D$_2$O are shown in FIGS. 5, 6, 7 and 8 respectively (400 MHz, δppm, JEOL GX-400).

As described above, each TAN-866 has three moles of ornithine among its constitute amino acids. From these results and their $^1$H NMR spectral data, it is estimated that TAN-866 A and B have three $N^5$-acetyl-$N^5$-hydroxy-ornithine and TAN-866 C and D have two $N^5$-acetyl-$N^5$-hydroxy-ornithine and a $N^5$-propionyl-$N^5$-hydroxy-ornithine. It is known that the N-hydroxyl group of said amino acids changes to N-hydroxyanion

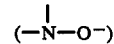

in the presence of trivalent iron ion and such iron ion is liganded by three N-hydroxyanion (J. Antibiotics, 24, 830, 1974).

When TAN-866 A is stirred or allowed to stand in a basic aqueous solution at 20° to 60° C., preferably 25° to 50° C., for 30 minutes to 8 hours, preferably 1 to 4 hours, the lactone bond of TAN-866 A molecule is hydrolyzed to give its carboxylic acid form compound ($C_{51}H_{83}N_{13}O_{20}FeNa$). The thus hydrolyzed compound can be isolated and purified as its monosodium salt using a chromatography on Diaion HP-20 etc.

Deacyl TAN-866 A ($C_{41}H_{68}N_{13}O_{19}Fe$) is obtained by hydrolysis of the above obtained carboxylic acid form compound with an amidase which is contained in the bacterial cells of *Pseudomonas acidovorans* IFO 13582. This hydrolysis is conducted in a phosphate buffer of pH 3 to 9, preferably pH 5 to 8, at 25° to 45° C., preferably 30° to 40° C. for 5 to 30 hours, preferably 10 to 25 hours. The amidase is used in an amount of 5 to 15 times, preferably 8 to 12 times the weight of the substrate. When the said enzyme is used for the reaction, the bacterial cells are supplied either as they are or in the form, previously treated with acetone etc.

Physical and chemical properties of deacyl TAN-866 A, which was obtained in Example 5, are as follows:

(1) Appearance: Reddish orange solid
(2) Molecular weight: m/z 1103 (M+H)+ (SI-MS method)
(3) Elemental analysis (%) (calculated as containing 7 moles of water)

|         | C     | H    | N     | O     | Fe   |
|---------|-------|------|-------|-------|------|
| Found:  | 40.19 | 6.37 | 14.34 |       | 4.0  |
| Calcd.: | 40.07 | 6.72 | 14.82 | 33.85 | 4.54 |

(4) Molecular formula: $C_{41}H_{68}N_{13}O_{19}Fe$
(5) Visible absorption spectrum (in methanol): $\lambda$max 422±3 nm ($E_{1\,cm}^{1\%}$=26±5)
(6) Infrared absorption spectrum: in KBr Main absorptions are as follows. 3380, 3070, 2950, 1660, 1590, 1540, 1470 1380, 1240, 1050, 980, 790, 730, 560 (cm$^{-1}$)
(7) Solubility: Soluble: water, dimethylsulfoxide, methanol Sparingly soluble: ethylacetate, chloroform
(8) Classification of substance: amphoteric substance TAN-866 B, C and D give the corresponding deacyl TAN-866 B, C and D by a method similar to that for production of deacyl TAN-866 A. The data of HPLC and SI-MS of those compounds are as follows:

TABLE 2

| Deacyl-TAN-866 | A | B | C | D |
|---|---|---|---|---|
| HPLC* (rt) (retention time) | 3.3 min. | 3.2 min. | 5.2 min. | 5.0 min. |
| SI-MS (M + H)+ | 1103 | 1119 | 1117 | 1117 |

*Column: ODS, YMC-Pack A-312
Mobil phase: 8% acetonitrile/0.01 M phosphate buffer (pH 6.3)
Flow rate: 2 ml/min
Detection: 214 nm Composition of constituent amino acids of these deacyl compounds are all identical with those of the corresponding TAN-866 A, B, C and D.

According to the above data and the method described below, the chemical formulae of TAN-866 and deacy TAN-866 were determined as shown in the formulae [I] and [II] respectively. Namely, it is determined based on the subtracted data by the SI-MS method from TAN-866 to the corresponding deacyl TAN-866 and $^1$H NMR spectrum [COSY method ($^1$H-$^1$H)] of iron-free TAN-866 that the fatty acid portion of TAN-866 is represented by the formula of $CH_3(CH_2)_5CH=CHCH_2CO—$. The sequence of the amino acids containing C- and N-terminal amino acids was determined by subjecting each deacyl TAN-866 to an amino acid sequencer. The binding position of the lactone group was determined by the NOESY Method in the $^1$H NMR spectrum of TAN-866 as shown in the formula [I].

The biological characteristics of TAN-866 and its iron-free compounds are described as follows. The antibacterial activities of TAN-866 are as shown in Table 3.

TABLE 3

| Test Organism | Minimal Inhibitory Concentration (μg/ml) (Note 1) TAN-866 | | | |
|---|---|---|---|---|
| | A | B | C | D |
| Staphylococcus aureus FDA 209P | >100 | >100 | >100 | >100 |
| Micrococcus luteus IFO 12708 | >100 | >100 | >100 | >100 |
| Bacillus subtilis NIHJ PCI 219 | >100 | >100 | >100 | >100 |
| Bacillus cereus FDA 5 | >100 | >100 | >100 | >100 |
| Escherichia coli NIHJ JC 2 | 3.13 | 6.25 | 12.5 | 3.13 |
| Salmonella typhimurium IFO 12529 | 0.39 | 0.39 | 0.39 | 0.39 |
| Citrobacter freundii IFO 12681 | 6.25 | 12.5 | 12.5 | 25 |
| Klebsiella pneumaniae IFO 3317 | 0.78 | 0.78 | 12.5 | 3.13 |
| Serratia marcescens IFO 12648 | >100 | >100 | >100 | >100 |
| Proteus mirabilis ATCC 21100 | >100 | >100 | >100 | >100 |
| Proteus vulgaris IFO 3988 | >100 | >100 | >100 | >100 |
| Proteus morganii IFO 3168 | >100 | >100 | >100 | >100 |
| Pseudomonas aeruginosa IFO 3080 | 3.13 | 3.13 | 12.5 | 3.13 |
| Alcaligenes faecalis IFO 13111 | >100 | >100 | >100 | >100 |
| Acinetobacter calcoaceticus IFO 13006 | >100 | >100 | >100 | >100 |

(Note 1)
Medium composition
Bacto Antibiotic Medium 3 (Difco Laboratories, USA): 17.5 g
Bacto yeast extract (Difco Laboratories, USA): 5.0 g
Bacto agar (Difco Laboratories, USA): 20 g
Distilled water (pH unadjusted): 1000 ml
Inoculum size: a loopful of approx. $10^6$ CFU/ml Table 4 shows the therapeutic effects of TAN-866 and its iron-free compounds to experimental infectious diseases in mice using *Pseudomonas aeruginosa* P-9, by subcutaneous administration.

TABLE 4

| Compound | ED$_{50}$ (mg/kg)* |
|---|---|
| TAN-866A | 0.57 |
| TAN-866B | 0.593 |
| TAN-866C | 0.590 |
| TAN-866D | 0.197 |
| TAN-866A iron-free compound | 0.44 |

*Total of three dosages

No acute toxicity of TAN-866A in mice was observed by intraperitoneal or oral administration in a dose of 1000 mg/kg.

As clearly shown in these data, TAN-866 and its iron-free compounds have antibacterial activity, mainly against gram-negative bacteria while showing no toxicity in mammals for instance. Therefore, TAN-866 or its iron-free compounds can be used in the therapeutics of bacterial infections in humans and domestic animals (e.g. cows, horses, pigs, etc.), domestic fowls (e.g. chickens, etc.), etc.

For using TAN-866 or its iron-free compounds as therapeutic drugs of, for example, infectious diseases by *Pseudomonas aeruginosa*, they are administered as, for example, injections dissolved in physiological saline parenterally, subcutaneously or intramuscularly at a dose of 0.1~20 mg/kg/day, preferably 0.5~10 mg/kg/day. And, TAN-866 or its iron-free compounds are prepared into capsules by mixing with lactose and administered at a dose of 0.5~100 mg/kg/day, preferably 2~50 mg/kg/day in terms of TAN-866 or an iron-free compound thereof.

Deacyl TAN-866 has an amino group and a carboxylic group as the derivatizable functions, which can easily be afforded N-acyl derivatives by reacting with acid halides such as fatty acid halides of carbon number 1 to 20 (e.g. myristyl chloride, linoleinyl chloride or capryl chloride) in week base solution. Thus obtainable N-acylated compounds are lactonized by the condensation reagents, for example, DCC in proper solvents (e.g. DMF) or by acidifying the reaction solutions. The new compounds thus obtained may be assumed to appear antimicrobial activities against *Pseudomonas aeruginosa*, for example. Thus, TAN-866 and deacyl TAN-866 are also promising as the starting materials and intemediates for the synthesis of novel medicinal products.

The following examples will describe the present invention in more detail, but are not intended to limit the invention thereto. Unless otherwise specified, % means weight/volume %.

EXAMPLE 1

Five hundred ml of a medium prepared by adding 0.5% precipitating calcium carbonate to an aqueous solution (pH 7.0) containing 2% glucose, 3% soluble starch, 1% raw soybean flour, 0.3% corn-steep liquor, 0.5% Polypepton (Daigo Nutritive Chemicals, Ltd.) and 0.3% sodium chloride in a 2 l Sakaguchi flask was inoculated with *Pseudomonas fluorescens* YK-310 (FERM BP-1369; IFO 14516) grown on an nutrient agar slant, which was subjected to reciprocal shaking culture at 24° C. for 48 hours. With the entire quantity of the resulting culture broth was inoculated 120 l of a medium prepared by adding 0.05% Actocol (Takeda Chemical Industries, Ltd.), an antifoaming agent, to the above-mentioned medium in a 200 l tank. Cultivation was carried out at 24° C. under aeration of 120 l/min. and agitation at 180 rpm for 48 hours. With 50 l of the resulting culture broth was inoculated 1200 l of a medium prepared by adding 0.05% Actocol to an aqueous solution (pH 6.5) containing 2% glycerol, 0.5% glucose, 0.5% Polypepton, 0.5% meat extract (Wako Pure Chemical Industries, Ltd.), 0.1% sodium chloride and 0.1% yeast extract (Daigo Nutritive Chemicals, Ltd.) in a 2000 l of tank. Cultivation was carried out at 17° C. under aeration of 1200 l/min. and agitation at 150 rpm for 42 hours.

The culture broth thus obtained was subjected to filtration by the aid of Hyflo Super-Cel (Johns Manville Sales Corp.). The filtrate (1300 l) was subjected to a column chromatography on Diaion HP-20 (50 l). The active substance was eluted with a 80% methanolic water (350 l). The eluate was concentrated, from which methanol was distilled off. The aqueous portion (30 l) was adjusted to pH 7, followed by extraction with isobutanol (20 l). The extract was washed with a 2% sodium bicarbonate solution, 0.05N hydrochloric acid, followed by concentration of the isobutanol layer. The concentrate (3 l) was added to n-hexane (10 l) to give precipitates. The supernatant was separated by decantation. To the remaining precipitates was further added n-hexane (3 l) to obtain a crude substance (21.1 g) containing TAN-866A. The crude substance (20.5 g) was dissolved in 50% methanolic water, and the solution was subjected to a column chromatography on Diaion HP-20 (50–100 mesh, 1 l). The column was washed with 60% methanolic water (6 l), then the antibiotic substance was eluted fraction-wise. The fractions were combined and concentrated. The concentrate was dissolved in a small volume of methanol, which was added to ether to give powdery product (532 mg). The powdery product (1 g) obtained by a similar procedure was subjected to a column chromatography on Sephadex LH-20 (1 l), eluting with methanol. The eluate was concentrated and the concentrate (530 mg) was dissolved in water (10 ml), which was purified by means of a chromatography on Diaion HP-20 (50–100 mesh, 200 ml). Thus obtained purified powder (274 mg) was assumed to be a mixture of closely analogous compounds by the peak pattern of HPLC. The powdery product (250 mg) was then subjected to reversed-phase HPLC for separation (column: YMC-PAK SH343; mobile phase: 30% acetonitrile/water) to collect the peak portion of the principal component, which was concentrated to yield reddish orange powder (64 mg) of TAN-866A.

EXAMPLE 2

On a scale similar to that in Example 1, cultivation, filtration, HP-20 column chromatography and isobutanol extraction were carried out, followed by subjecting the concentrate (3 l) of the extract solution to chromatography on silica gel (1.5 l). The column was washed with isobutanol (4.5 l), isopropanol (4.5 l) and isopropanol:methanol (1:1) (4.5 l), followed by elution with methanol (4.5 l). The eluate was concentrated to dryness to give a powdery product (10.6 g). It was quantitatively determined by means of HPLC that the powdery product contained TAN-866A (3.5 g).

Then, 31 g of the powdery product obtained by similar procedure to the above was dissolved in 50% methanolic water (1 l), and the solution was subjected to a column chromatography on Diaion HP-20 (100~200 mesh, 1 l). The columnm was washed with 50% methanolic water (3 l) and 60% methanolic water (1 l), followed by fractionately eluting the antibiotic substance with 70% methanolic water (3 l) and 75% methanolic water (2 l). Each fraction was concentrated and lyophilized, yielding Powder I (content of A: 67%, 7.6 g), Powder II (content of TAN-844 A: 48%, 8.0 g) and Powder III (content of TAN-866 A: 34%, 4.4 g).

Then, the Powder I (7.5 g) was subjected to preparative reserved-phase HPLC. From the column was eluted the antibiotic substance with a solvent system of a 32% aqueous solution of acetonitrile using YMC-PAK R-355 (25/44) (Yamamura Chemical Laboratories). Each fraction was subjected to HPLC for analysis to determine the amount of each component quantitatively, followed by concentration and lyophilization to obtain the powder (1.7 g) containing TAN-866 A and B, the powder (2.2 g) containing solely TAN-866 A and the powder (0.33 g) containing TAN-866 A, C and D. The powder containing TAN-866 A and B was again subjected to preparative HPLC (column: YMC-PAK S-363 I-15, the solvent system: the same as in the above-mentioned HPLC for separation) to thereby isolate TAN-866 A (1.15 g) and TAN-866 B (209 mg) as reddish orange powder. The powder containing TAN-866 A, C and D was similarly processed to obtain TAN-866 C (70 mg) and TAN-866 D (150 mg) as reddish orange powder.

EXAMPLE 3

In water (2 ml) was dissolved the purified powder (40 mg) of TAN-866A obtained in Example 1, to which was added a solution of 8-hydroxyquinoline (40 mg) in methanol (2 ml). The reaction solution was allowed to stand at 4° C. for 15 hours. The resulting black precipitates were filtered off with a filter paper. Methanol in the filtrate was distilled off, followed by addition of water (20 ml), which was washed with chloroform (10 ml) four times. The aqueous portion was concentrated and lyophilized to obtain an iron-free compound (29 mg) of TAN-866A as white powder.

Molecular formula: $C_{51}H_{85}N_{13}O_{19}$

Elemental analysis (%): (samples dried over phosphorus pentoxide at 60° C. for 8 hours, calculated as containing 3 mol. of water.

|   | Found | Calcd. |
|---|---|---|
| C, | 49.33 | 49.47 |
| H, | 7.45 | 7.41 |
| N, | 14.78 | 14.70 |
| O, |  | 28.42 |

Molecular weight determined: by SI-MS method m/z 1184 $(M+H)^+$

UV spectrum: (in water) End absorption

IR spectrum: (in KBr) main absorptions are shown 3300, 2930, 1640, 1520, 1230, 570 $(cm^-)$

EXAMPLE 4

By a procedure similar to that in Example 3, starting from purified powdery products of TAN-866 B, C, D (20 mg, 10 mg, 20 mg, respectively) obtained in Example 2, iron free compounds of TAN-866 B, C and D were obtained as white powdery products (20 mg, 8 mg and 19 mg, respectively). TAN-866 B iron-free compound:

Molecular formula: $C_{51}H_{85}N_{13}O_{20}$

Elemental analysis (%): (samples dried over phosphorus pentoxide at 60° C. for 8 hours, calculated as containing 2.5 mol. of water)

|   | Found | Calcd. |
|---|-------|--------|
| C, | 49.03 | 49.19 |
| H, | 7.24  | 7.28  |
| N, | 14.59 | 14.62 |

Molecular weight determined: by SI-MS method m/z 1200(M+H)+

UV spectrum: (in water) End adsorption

IR spectrum: (in KBr) main absorptions are shown 3330, 2940, 1665, 1530, 1240, 590 (cm−)

TAN-866 C iron free compound:

Molecular formula: $C_{52}H_{87}N_{13}O_{19}$

Elemental Analysis (%): (samples dried over phosphorus pentoxide at 60° C. for 8 hours, calculated as containing 3.5 mol. of water)

|   | Found | Calcd. |
|---|-------|--------|
| C, | 49.36 | 49.51 |
| H, | 7.21  | 7.35  |
| N, | 14.26 | 14.38 |

Molecular weight determined: by SI-MS method m/z 1198 (M+H)+

UV spectrum: (in water) End adsorption

IR spectrum: (in KBr) main absorptions are shown 3300, 2940, 1665, 1530, 1235, 590 (cm−)

TAN-866 D iron-free compound:

Molecular formula: $C_{52}H_{87}N_{13}O_{19}$

Elemental analysis (%): (samples dried over phosphorus pentoxide at 60° C. for 8 hours, calculated as containing 3 mol. of water)

|   | Found | Calcd. |
|---|-------|--------|
| C, | 49.71 | 49.87 |
| H, | 7.22  | 7.48  |
| N, | 14.41 | 14.54 |

Molecular weight determined: by SI-MS method m/z 1198 (M+H)+

UV spectrum: (in water) End absorption

IR spectrum: (in KBr) main absorptions are shown in 3400, 2940, 1665, 1530, 1240, 590 (cm−)

EXAMPLE 5

In 0.05M phosphate buffer (pH9, 150 ml) was dissolved TAN-866 A (150 mg), and agitated at 40° C. for 2 hours. The reaction solution was subjected to a column chromatography on Diaion HP-20 (20 ml), and the elution was conducted with 50% methanolic water. The eluate was concentrated to dryness to yield a sodium salt of carboxylic acid form compound of TAN-866 A. SI-MS: m/z 1277 (M+H)+, Molecular formula: $C_{51}H_{83}N_{13}O_{20}FeNa$ The thus obtained carboxylic acid form compound (150 mg) was added to 0.05M phosphate buffer (pH 7, 150 ml) containing crude amidase (1.5 g) which was yielded by a *Pseudomonas acidovorans* IFO 13582, and then stirred at 37° C. for 18 hours. The reaction solution was centrifuged, and the obtained supernatant was adjusted to pH 2.5, followed by extraction with ethyl acetate. This extract solution contained the fatty acid. The aqueous layer was subjected to a column chromatography on Diaion HP-20 (50–100 mesh, 30 ml). The column was fractionately eluted with 5–20% methanolic water. The fractions containing a peptide were concentrated to dryness to yield deacyl TAN-866 A as reddish orange powder (97 mg).

EXAMPLE 6

TAN-866 B (10 mg), TAN-866 C (2 mg) and TAN-866 D (10 mg) was hydrolyzed by a method similar to that in Example 5 to yield deacyl TAN-866 B (5 mg), deacyl TAN-866 C (1.5 mg) and deacyl TAN-866 D (5.7 mg), respectively.

What we claim is:

1. A compound of the formula, or an iron-free compound thereof:

$$CH_3(CH_2)_5-CH=CH-CH_2-CONH-$$

[structural formula of cyclic peptide with Fe coordination, containing R1, R2, R3, R4 substituents]

wherein $R_1$ is H or OH and each $R_2$, $R_3$ and $R_4$ is H or $CH_3$.

2. The compound according to claim 1, wherein each $R_1$, $R_2$, $R_3$ and $R_4$ is H.

3. The compound according to claim 1, wherein $R_1$ is OH and each $R_2$, $R_3$ and $R_4$ is H.

4. The compound according to claim 1, wherein $R_1$ is H, any two of $R_2$, $R_3$ and $R_4$ are H and the other is $CH_3$, and the retention time of HPLC is 5.8 minutes.

5. The compound according to claim 1, wherein $R_1$ is H, any two of $R_2$, $R_3$ adn $R_4$ are H and the other is $CH_3$, and the retention time of HPLC is 6.2 minutes.

* * * * *